(12) United States Patent (10) Patent No.: US 9,095,803 B2
Augustine et al. (45) Date of Patent: Aug. 4, 2015

(54) NECK-WORN AIR FILTRATION DEVICE

(75) Inventors: Scott D. Augustine, Bloomington, MN (US); Mark C. Albrecht, Minneapolis, MN (US); Randall C. Arnold, Minnetonka, MN (US); Ryan S. Augustine, Minneapolis, MN (US); Ryan Barrows, Maple Grove, MN (US); Andrew McGregor, Minnetonka, MN (US)

(73) Assignee: Augustine Biomedical and Design, LLC, Eden Prairie, MN (US)

( * ) Notice: Subject to any disclaimer, the term of this patent is extended or adjusted under 35 U.S.C. 154(b) by 766 days.

(21) Appl. No.: 13/158,861

(22) Filed: Jun. 13, 2011

(65) Prior Publication Data

US 2011/0315142 A1 Dec. 29, 2011

Related U.S. Application Data

(63) Continuation of application No. 12/037,079, filed on Feb. 25, 2008, now abandoned.

(60) Provisional application No. 60/891,395, filed on Feb. 23, 2007, provisional application No. 60/891,400, filed on Feb. 23, 2007, provisional application No. 60/891,707, filed on Feb. 26, 2007.

(51) Int. Cl.
*B01D 46/02* (2006.01)
*A61M 16/10* (2006.01)
(Continued)

(52) U.S. Cl.
CPC ........... *B01D 46/02* (2013.01); *A61M 15/0083* (2014.02); *A61M 16/0875* (2013.01); *A61M 16/105* (2013.01); *A61M 16/107* (2014.02); *A61M 16/1055* (2013.01); *A61M 15/08* (2013.01); *A61M 16/108* (2014.02);
(Continued)

(58) Field of Classification Search
CPC ............... B01D 46/02; A61M 16/105; A61M 16/1055; A61M 16/107
USPC ........... 55/363, 364, 372, 374, 375, 376, 377, 55/385.1, 467, 473, DIG. 29
See application file for complete search history.

(56) References Cited

U.S. PATENT DOCUMENTS

| 96,989 A | 11/1869 | Somes |
|---|---|---|
| 2,025,659 A | 12/1935 | Gilquin |

(Continued)

FOREIGN PATENT DOCUMENTS

| EP | 0624340 | 12/1998 |
|---|---|---|
| JP | 2005111048 | 4/2005 |

(Continued)

OTHER PUBLICATIONS

PCT Application No. PCT/US2008/054928, International Search Report and Written Opinion, dated Jul. 11, 2008, 10 pages.

(Continued)

*Primary Examiner* — Robert Clemente
(74) *Attorney, Agent, or Firm* — Fredrikson & Byron, P.A.

(57) ABSTRACT

A neck-worn personal air filtration device for providing a zone of filtered air around or near a user's breathing zone is described. The device comprises a blower, a hose, and a neck-worn plenum including a filter. Air blown from the blower, passes through the hose and into the plenum exiting the plenum. The air is filtered by a filter for breathing by the user.

20 Claims, 5 Drawing Sheets

(51) Int. Cl.
  *A61M 16/08* (2006.01)
  *A61M 15/00* (2006.01)
  A61M 15/08 (2006.01)
  A61M 16/14 (2006.01)
  A61M 16/16 (2006.01)

(52) U.S. Cl.
  CPC .............. *A61M 16/14* (2013.01); *A61M 16/16* (2013.01); *A61M 2205/42* (2013.01)

(56) References Cited

U.S. PATENT DOCUMENTS

| | | |
|---|---|---|
| 3,266,064 A | 8/1966 | Figman |
| 3,653,083 A | 4/1972 | Lapidus |
| 3,724,172 A | 4/1973 | Wood |
| 3,820,536 A | 6/1974 | Anspach, Jr. |
| 3,941,697 A | 3/1976 | Johnson |
| 4,391,009 A | 7/1983 | Schild et al. |
| 4,398,535 A | 8/1983 | Guibert |
| 4,818,122 A | 4/1989 | Arbuthnot |
| 4,977,634 A | 12/1990 | Koji |
| 5,160,517 A | 11/1992 | Hicks et al. |
| 5,247,714 A | 9/1993 | Lipps |
| 5,304,213 A | 4/1994 | Berke |
| 5,305,483 A | 4/1994 | Watkins |
| 5,312,465 A | 5/1994 | Riutta |
| 5,317,767 A | 6/1994 | Hargest |
| 5,389,037 A | 2/1995 | Hale |
| 5,588,698 A | 12/1996 | Hsueh |
| 5,733,320 A | 3/1998 | Augustine |
| 5,785,723 A | 7/1998 | Beran |
| 5,876,428 A | 3/1999 | Van Duren |
| 5,902,365 A | 5/1999 | Haggard |
| 6,230,350 B1 | 5/2001 | Goldstein |
| 6,261,332 B1 | 7/2001 | Richard |
| 6,440,157 B1 | 8/2002 | Shigezawa |
| 6,447,538 B1 | 9/2002 | Van Duren |
| 6,702,662 B2 | 3/2004 | Kristensson |
| 6,988,293 B2 | 1/2006 | Ritter |
| 7,037,068 B2 | 5/2006 | Cobb |
| 7,037,188 B2 | 5/2006 | Schmid |
| 7,063,087 B2 | 6/2006 | Cerbini |
| 7,118,608 B2 | 10/2006 | Lovell |
| 7,195,660 B2 | 3/2007 | Little |
| 7,279,021 B2 | 10/2007 | Haberlein |
| 7,370,380 B2 | 5/2008 | DeFranks |
| 7,607,433 B2 | 10/2009 | Silva |
| 2003/0033790 A1 | 2/2003 | Hague |
| 2003/0036786 A1 | 2/2003 | Duren et al. |
| 2003/0084510 A1 | 5/2003 | Lin |
| 2003/0089233 A1 | 5/2003 | Borla |
| 2003/0150328 A1 | 8/2003 | Hansson |
| 2004/0112381 A1 | 6/2004 | Ujhazy |
| 2004/0244595 A1 | 12/2004 | Elliot |
| 2005/0229557 A1 | 10/2005 | Little |
| 2006/0271134 A1 | 11/2006 | Frey |
| 2007/0240719 A1 | 10/2007 | Duarte |
| 2008/0020695 A1 | 1/2008 | Chang |

FOREIGN PATENT DOCUMENTS

| | | |
|---|---|---|
| WO | 9711625 | 4/1997 |
| WO | 2005027699 | 3/2005 |

OTHER PUBLICATIONS

Avidan et al., "Convection Warmers, Not Just Hot Air", Anaesthesia, 1997, pp. 1073-1076, 52, Blackwell Science Ltd.

PCT/US2009/036260, Invitation to Pay Additional Fees and Partial International Search Report, dated Jul. 10, 2009.

PCT Application No. PCT/US2009/059721, International Search Report and Written Opinion, dated Nov. 17, 2009, 7 pages.

NECK-WORN AIR FILTRATION DEVICE

PRIORITY CLAIM

The present application is a continuation of U.S. patent application Ser. No. 12/037,079, entitled NECK-WORN AIR FILTRATION DEVICE, filed Feb. 25, 2008, which claims priority to provisional application Ser. No. 60/891,395, entitled PERSONAL AIR FILTRATION DEVICE filed on Feb. 23, 2007; Ser. No. 60/891,400, entitled PERSONAL AIR FILTRATION DEVICE filed on Feb. 23, 2007; and Ser. No. 60/891,707, entitled PERSONAL AIR FILTRATION DEVICE filed on Feb. 26, 2007, each of which are incorporated by reference in their entireties herein.

TECHNICAL FIELD

The present invention is related to air filtration devices. In particular the invention is related to air filtration devices worn by an individual and which provide filtered air to a space adjacent to or near the individual's face.

BACKGROUND

It is estimated that 1 in 5 Americans suffer from allergic rhinitis/conjunctivitis (AR). AR is the result of an IgE mediated immune system response to inhaled aero-allergens, which typically include dust mite, fungi, animal dander, pollutants, molds, and pollens. For those individuals afflicted by AR, the short term effects extend beyond the physical symptoms found in the eyes and nose, often resulting in cognitive impairment, sleep disturbance, lowered work/school productivity, and reductions in quality of life. More alarmingly, if AR symptoms persist on a long term basis the disease can lead to the development of comorbities, including asthma, sinusitis, otiis media, nasal polyposis, lower respiratory tract infection, and dental malocclusion. Typical treatment for AR consists of three steps. First, the trigger allergen(s) is identified and environmental control measures are employed to minimize allergen exposure. Second, if elimination steps are unsuccessful, medication is employed to manage and control symptoms. Third, for perennial allergen exposure, immunotherapy may be undertaken to obtain long term symptom control. Allergen avoidance is the preferred treatment, providing symptom resolution absent medication. But to date few allergen avoidance measures exist that reduce airborne allergen concentrations to a clinically relevant level.

Effective allergen avoidance focuses on two basic principles: identification of the offending allergen source, and removal/elimination of the offending source or reduction of the concentration of inhaled aero-allergens. Commonly practiced allergen avoidance measures that are clinically effective include pet removal from the home and geographic re-location. Other forms of allergen avoidance that are of questionable clinical effectiveness but are commonly practiced include whole room air filtration, dust mite casings, use of air conditioning, and carpet removal.

Of the listed allergen avoidance measures, air filtration systems, some of which remove particulates at 99.97% efficiency, show great promise for reducing inhaled aero-allergen concentrations to a clinically relevant level. However, the current practice of such technologies limit their effectiveness. For example, people often utilize room air cleaner units in an attempt to achieve a reduction in particle levels within a localized area. These types of units effectively remove a high percentage of harmful particles from the air that flows through the unit. However, individuals within the area of the unit may not experience all of the beneficial results of this particle removal because the air that is discharged from the unit is able to pick up additional harmful particles from the surrounding environment prior to reaching and being breathed in by the individuals. Furthermore, the effectiveness of air cleaners and purifiers is greatly affected by the size of the room, such that results worsen as the room size increases. Other room factors such as air-tightness, the presence of air currents and traffic which can kick up particles, also affect the performance of air cleaners and purifiers. In the case of dust mites residing in bedding, a room air filter can not adequately reduce the allergenic exposure between the bedding and the person sleeping in the bed. Given these factors, it is difficult for an air cleaner or purifier to significantly reduce the levels of allergens and pollutants being breathed by an individual. Prior art air cleaners have attempted to reduce these problems by directing air directly into the face of a sleeping person. Such devices must blow a considerable wind on to the sleeping person's head in order to prevent ambient particles from circulating near the person while sleeping. Such high wind levels may be annoying to a person who is trying to sleep. Furthermore, many of these devices are cumbersome, expensive and unsightly.

SUMMARY

In one aspect, the invention provides a neck-worn personal air filtration device. A blower coupled to a plenum by a hose is adapted to provide an airflow through the hose to the plenum. The plenum is adapted to be worn about a user's neck.

In certain embodiments, neck-worn personal air filtration device comprises an upper and lower surfaces, at least a portion of the upper surface being air permeable. A filter is disposed within the device such that the airflow provided by the blower passes through the filter prior to or as the airflow is caused to exit the plenum through the air permeable surface. Embodiments may include, for example, a U-shaped plenum to be worn about the user's neck or a bib-shaped plenum to be worn on the user's chest and draped about the user's neck. Moreover, in some embodiments, the filter may be a point of delivery filter.

In another aspect the invention includes a method of providing filtered air to an area around a user's head. A blower and plenum are provided. The blower being adapted to deliver air to the plenum, and the plenum having upper and lower surfaces, at least a portion of the upper surface being air permeable and including a filter. The plenum is positioned proximate the user's head, and air is delivered to the plenum, thereby causing the air to pass through the filter and into the area around the user's head.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Those skilled in the art will recognize that many of the examples provided have suitable alternatives that can be utilized.

Embodiments of the invention comprise a device and method for providing an area of filtered air adjacent to or near the face head of a person without blowing a high volume of air toward the face. A plenum, through which air can be filtered, is placed near the user's head. The plenum can deliver filtered air to the space next to or near the user's face eliminating the need to filter the air of the entire room and making filtration more efficient. In addition, by minimizing the time and distance between the release of the air from the filter and inhalation by the user, the amount of recontamination of the filtered air is decreased. Moreover, a zone of filtered air can be created using low air flow, reducing unwanted noise and the feeling of wind blowing in the sleeping person's face.

Figure 1:
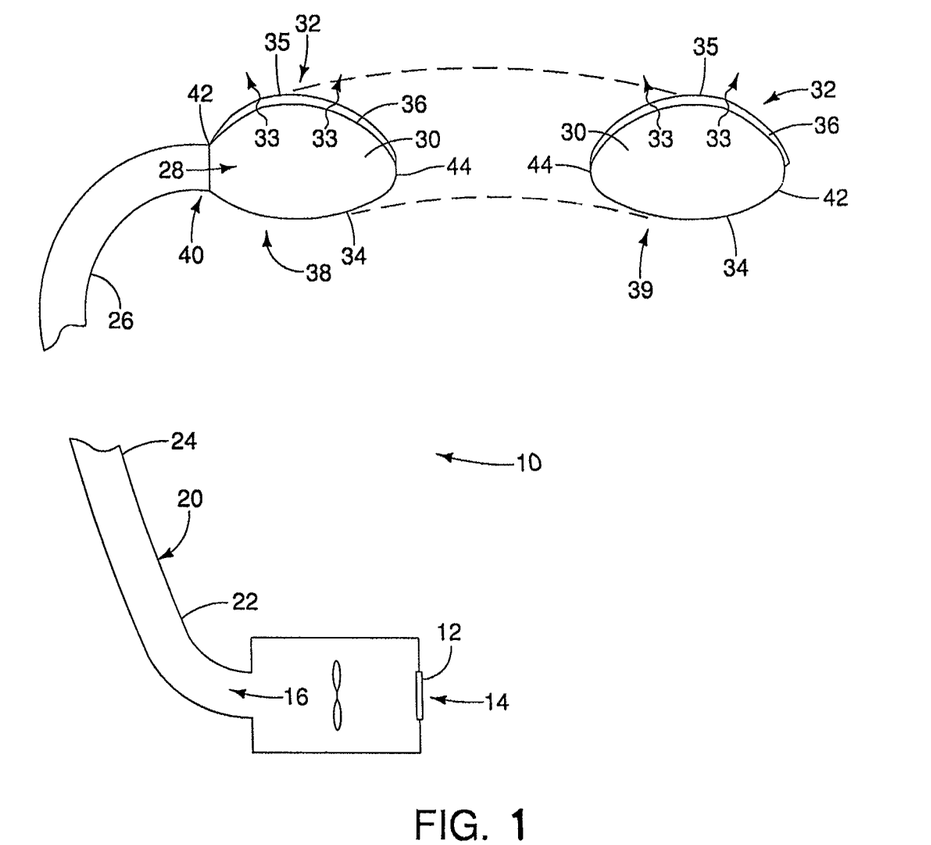
FIG. 1 is a cross sectional view of a personal air filtration system according to embodiments of the invention.

Embodiments of the personal air filtration device 1, as shown in FIG. 1, can include a blower 10, a hose 20, and a plenum 30. Blower 10 includes an air intake port 12, and an air delivery port coupled to the hose 20. The blower 10 may be placed in proximity to user, such as next to a chair in which the user is sitting or next to a bed on which the user is lying. The blower 10 is preferably small to allow for easy transportation and concealment, and is also preferably quiet so that the noise is not disruptive. Quiet functioning of the system may be particularly desirable when the personal air filtration device 1 is used as part of relaxation, such as in a spa, a salon or at home. Optionally, the blower 10 can include a component which produces white noise to obscure any noise produced by the blower 10. Other optional features which may be included in the blower 10 include a temperature control to heat or cool the air, an air humidifier, a medication dispenser, and/or an aroma dispenser. These optional features may be controlled manually or automatically, such as by a timing mechanism. Some blowers may include one or more air filters disposed at one or more locations within the blower or at an air intake or delivery ports.

The blower 10 can be attached to a hose 20. Hose 20 has a proximal section 22 which is attached to the blower 10, a distal section 26 which is attached to the plenum 30, and a middle section 24 connecting the proximal and distal sections 22, 26. The hose 20 may be comprised of a rigid or semi-rigid material to prevent collapse. Alternatively, the hose 20 may be comprised of a collapsible material, such as fabric or polymeric foam. Such a collapsible hose would inflate when air pressure is applied and would not feel like a hard object if touched by the user. In some embodiments, the hose 20 is composed of both a rigid or semi-rigid material and a collapsible material. For example, in one embodiment, the hose 20 is rigid in the proximal and middle sections 22, 24 and is collapsible in the distal section 26. Such a hose 20 may include semi-rigid support members near the plenum inlet 40. The hose may optionally include a formed elbow, such as to transition the airflow between a substantially vertical direction and a substantially horizontal direction.

Figure 2:
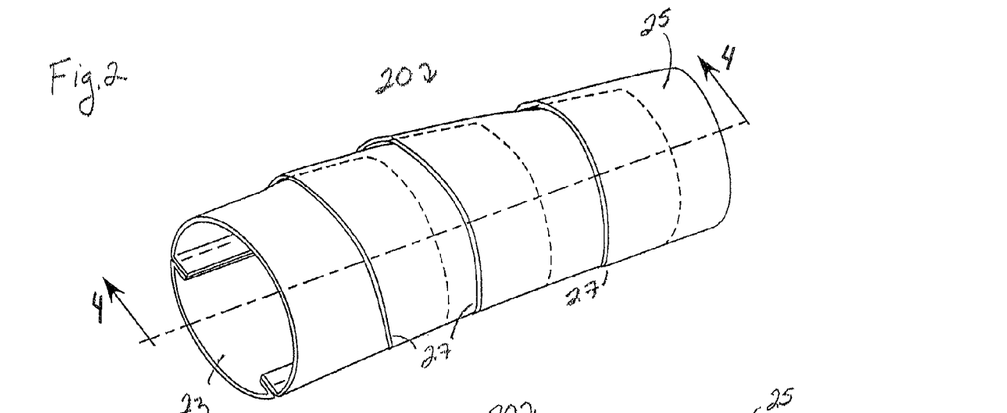
FIG. 2 is perspective view of a portion of a hose according to embodiments of the invention.
Figure 3:
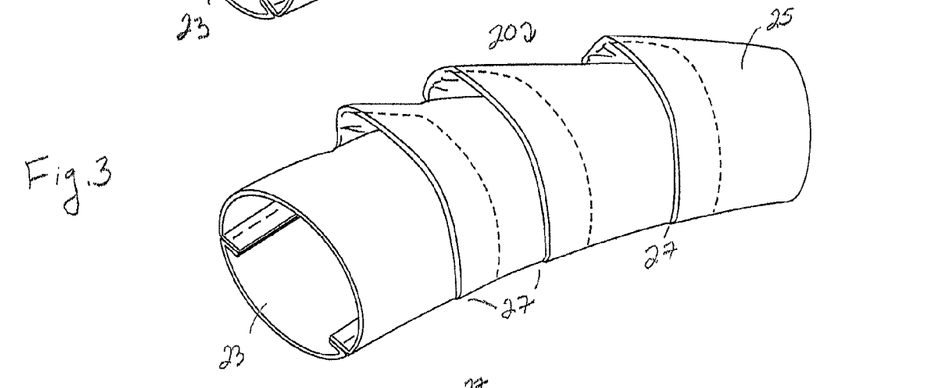
FIG. 3 is perspective view of a portion of a hose according to embodiments of the invention.
Figure 4:
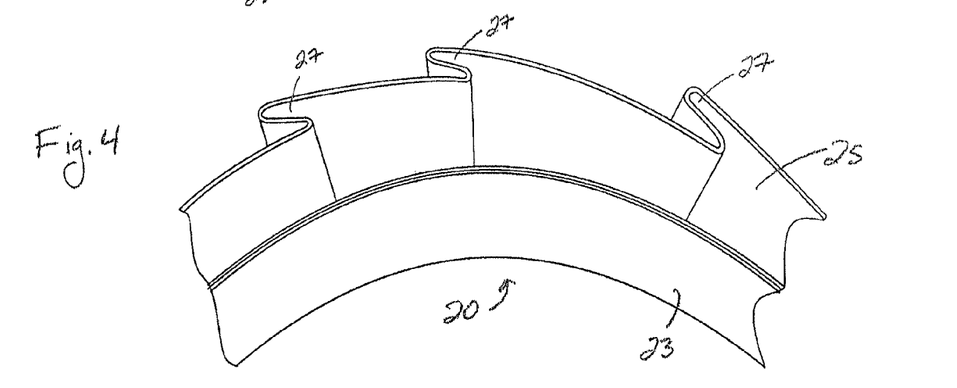
FIG. 4 is a cross sectional view of a portion of a hose according to embodiments of the invention.

In some embodiments, such as that shown in FIGS. 2 to 4, the hose 20 or a portion of the hose 20 is comprised of a flexible material such as an air impermeable fabric and includes pleats 27 to prevent the hose from collapsing when bent. The hose 20 includes a first surface 23 and a second surface 25. The width of the first surface 23 is less than that of the second surface 25, such that the second surface 25 forms a greater portion of the circumference of the hose than the first surface 23. The difference in widths of the first and second surfaces 23, 25 assists the second surface 25 in forming an arch relative the first surface 23, helping the hose to stay open and assisting with air flow.

The hose 20 may include pleats 27 over a portion or all of the hose 20. In the embodiment shown in FIGS. 2 to 4 the second surface 25 of the hose 20 is pleated relative to the first surface 23. The pleats 27 allow the hose 20 to bend without narrowing the space inside the hose 20, preventing the restriction of air flow when the hose 20 is bent. As shown in FIG. 2, when the hose 20 is straight, the pleats 27 in the second surface 25 of the hose 20 fold in upon themselves, shortening the length of the second surface 25. When the hose bends toward the first surface 23, the pleats 27 in the second surface 25 open up, allowing the second surface 25 to become longer such that the space within the hose 20 is not compressed. In some embodiments, the first surface 23 of the hose 20 lies adjacent to the bed and the pleats 27 extend over the elbow portion of the hose 20, allowing the hose 20 to bend without compressing or kinking.

Figure 7:
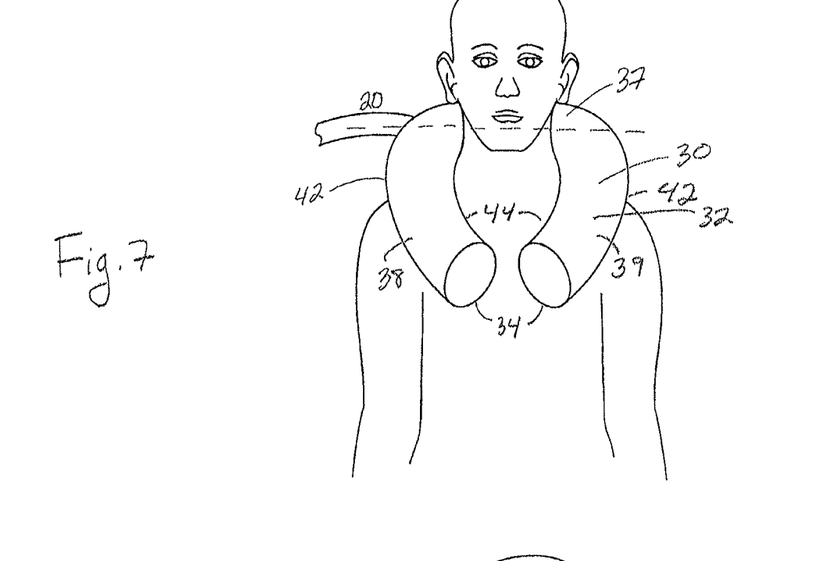
FIG. 7 is a perspective view of the plenum of FIG. 1.
Figure 8:
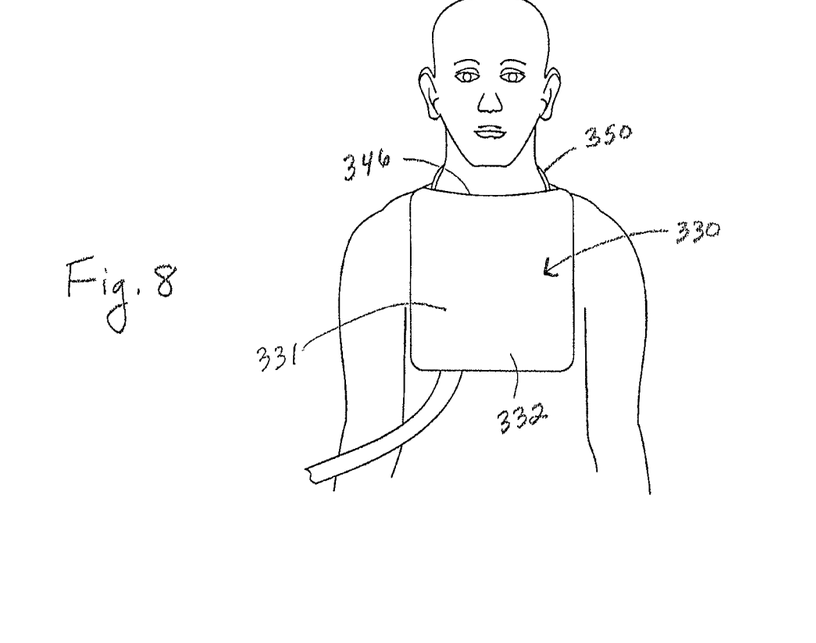
FIG. 8 is a perspective view of a bib shaped plenum according to embodiments of the invention.

The plenum may be formed into many different shapes and sizes. For instance, as described further below, the plenum is approximately U-shaped in the embodiment shown in FIGS. 1 and 7, and in the embodiment shown in FIG. 9. When in use, the U-shaped plenum 30 of FIG. 1 is inverted such that the bottom of the U is oriented behind the neck of the user and forms a neck portion 37 (see FIG. 7) of the plenum 30. In alternative embodiments, the plenum is shaped like a bib. An example of such an embodiment is shown in FIG. 8.

Referring back to FIG. 1, the distal section 26 of the hose 20 can be connected to the plenum 30 at the plenum inlet 40. The hose 20 may be permanently attached to the plenum inlet 40 or may be detachable from the plenum 30. The plenum 30 includes an upper or outward surface 32 which is adjacent to the user's head and through which air flows, and a lower or inward facing surface 34 which can be positioned adjacent to a user's body. The upper and lower surfaces 32, 34 of the plenum 30 are constructed of a flexible material. At least a portion of the upper surface 32 of the plenum 30 is partially or entirely air permeable while the lower surface 34 is generally air impermeable. Plenum 30 can be filled with air, supplied by the blower 10 through the hose 20. The air escapes from the plenum 30 through the upper surface 32, into the space adjacent to or near the user's face. In this way the personal air filtration device 1 can deliver air to the breathing space of the user without the need to deliver air to an entire room. Furthermore, air is delivered directly to the user's breathing space, avoiding contamination from nearby structures.

The upper surface 32 can be connected to the lower surface 34 of the plenum 30 along the edges of the plenum, such as by sewing, adhesive, or thermal bonding. Alternative embodiments may additionally include one or more panels connected between the top and bottom surface to change the profile of the plenum. Such panels can be connected by any suitable means and may comprise an air impermeable material, an air permeable material, or both. The plenum may be any shape, such as square, rectangular, round, oblong, U-shape, or a combination of shapes. The lower surface 34 of the plenum 30 generally rests on the body of the user. For example, it may lie on or against the user's neck, chest or shoulders. In one embodiment, the air impermeable surfaces of the present invention are constructed of micro fiber Polyester or coated Nylon Supplex coated both of which are available from Dupont.

The edges of the plenum 30 form a generally air tight connection between the upper and lower surfaces 32, 34 of the plenum 30. However, in some embodiments air inlet 40 is located between the upper and lower surfaces. In such embodiments, the air inlet 40 can form a gap in the connection between the upper and lower surfaces 32, 34 or any panels that may be between the upper and lower surfaces. The air inlet 40 provides a location for air to enter the plenum 30 from the hose 20. Alternatively, the air inlet 40 may be entirely within either the upper surface, lower surface, or other panels of the plenum.

In many embodiments, at least a portion of the upper surface 32 of the plenum 30 can include a filter 36. Air enters the blower 10 through the air intake 12 as shown by arrow 14. The blower 10 pushes air into the hose 20 as shown by arrow 16, through the hose and into the plenum 30 as shown by arrow 28. Air then accumulates within the plenum 30 and can exit though the air permeable portion of the upper surface 32 by passing through the filter 36, as shown by arrows 33. The air that exits the upper surface 32 of the plenum 30 is therefore filtered air resulting in a zone of filtered air about the head of the user. Filter 36 may be comprised of a material which provides HEPA (high efficiency particulate air) levels of filtration, such as Technostat® (available from Hollingsworth & Vose Company of East Walpole, Mass.).

By locating the filter 36 about the air permeable portion of the upper surface 32 of the plenum 30, the air is filtered through a large surface area. As a result, the pressure drop induced as the air traverses the filter 36 is much less than that caused by traversing a smaller surface area of the same filter material. By using a large surface area, the air can be filtered effectively at a low pressure. As a result of lower air pressure, air flow can be reduced, allowing the blower 10 to perform quietly while still producing an adequate volume of filtered air. Moreover, because the plenum 30 is located near the user's head, the relatively low air flow is effective to create a zone of filtered air about the user's head, and prevent unfiltered air from the environment from being inhaled by the user. Filters located where air flow leaves the plenum 30 (i.e. at the air permeable portion of the upper surface 32) can be classified as point of delivery filters. A point of delivery filter may be preferable because it allows for filtration of the air at the last possible moment, thereby eliminating contaminants that may have accumulated within the device itself e.g. in the hose, blower, etc.

Moreover, in some embodiments, the blower 10 (see FIG. 1) may include one or more filtration mechanisms (e.g. an ultraviolet radiation filter, a carbon-based filter, or a HEPA or other mechanical filter). An air intake filtration mechanism may be positioned proximate the air intake port 12 to filter air as it is drawn into the blower 10. Alternatively, or in addition, a filtration mechanism may be placed near the air outlet to filter the air as it leaves the blower 10. Embodiments including a blower 10 having a filtration mechanism may or may not include an additional filter positioned downstream of the blower. Embodiments that include an upstream filter, for example in the blower, instead of one further downstream, may allow relatively more contaminants present within the blower or hose to be passed into the user's breathing zone.

In some embodiments, the plenum 30 is a single air chamber. Alternatively, the plenum 30 may have multiple interconnected air chambers. For example, the plenum 30 could have one or more points of attachment between the upper surface 32 and the lower surface 34, such as near the periphery of the plenum 30 to form one or more manifolds. Alternatively, one or more manifolds may not comprise separate chambers but rather may be areas or passages within a plenum 30 which comprises a single air chamber.

Figure 5:
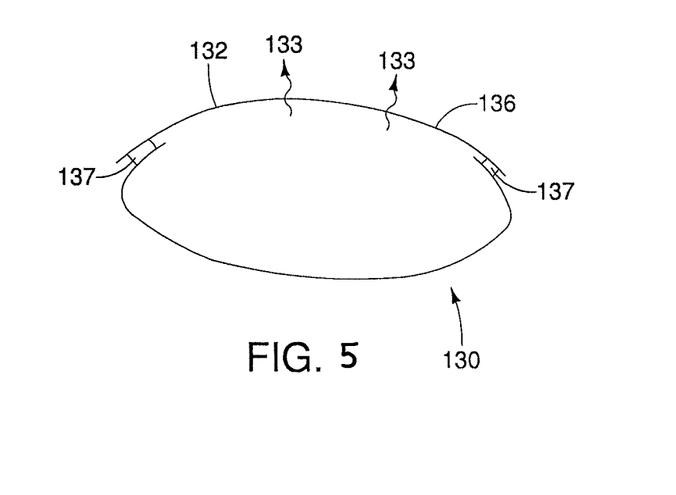
FIG. 5 is a cross sectional view of a plenum according to embodiments of the invention.
Figure 6:
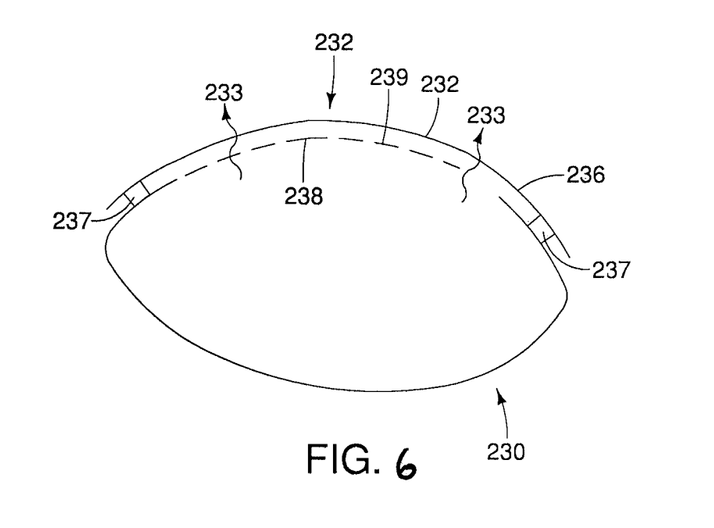
FIG. 6 is a cross sectional view of a plenum according to embodiments of the invention.

The filter may be incorporated into the plenum in a variety of ways. As shown in FIG. 1, the filter 36 itself forms the air permeable portion of the upper surface 32 of a plenum 30. The edges of the filter 36 form a permanent and air tight connection with the impermeable portions of the plenum. Alternatively, as shown in FIGS. 5 and 6, the filter 136, 236 may be removably attached to the air impermeable portions of the plenum 130, 230. The filter attachment element 137, 237 may be provided by adhesive, hook and loop fasteners such as Velcro, zippers, and/or other forms of attachment. By providing a removable filter 136, 236, the filter may be changed periodically as needed for washing or disposal and replacement of the filter 136, 236 without requiring replacement of the entire plenum 130, 230. Alternatively, the filters 136, 236 may be permanently attached to the plenum 130, 230 such as by permanent adhesive or sewing. In such embodiments, the entire plenum 130, 230 may be periodically washed or disposed of and replaced as needed.

In the embodiment shown in FIG. 5, the filter 136 forms the upper surface 132 of the plenum 130. A filter attachment element 137 is located near the edge of the filter 136 and forms a generally air tight connection between the filter 136 and the air impermeable portion of the plenum. Air exits the plenum 130 through the filter 136 as shown by arrows 133. In the embodiment shown in FIG. 6, the upper surface 232 of the plenum 230 includes a filter 236 which overlies an inner layer 238. In one embodiment, the inner layer 238 has apertures 239 to allow air to exit and may be comprised of an air impermeable material. After passing through the apertures 239, air passes through the filter 236 and exits the plenum 230 as filtered, clean air, as shown by arrows 233. In an alternative embodiment, the inner layer 238 is comprised of an air permeable material, potentially without apertures 239, such that air passes through the inner layer 238 and then through the filter 230 to exit the plenum.

In some embodiments, the filter material may be somewhat friable such that small fibers may break off of the filter surface. This may particularly be a problem when the filter comes into contact with the user. In addition, the user may find the feeling of the filter to be unfamiliar when it touches the user's skin. To prevent these problems, the plenum 30 may include a cover layer 35. An example of an embodiment including a cover layer 35 is shown in FIG. 1. The cover layer 35 lies over the filter 36, between the filter 36 and the user, and completely covers the filter 36. In this way, the cover layer 35 forms a barrier between the filter 36 and the user. The cover layer may feel more comfortable or more familiar to the user. It may also act as a barrier between the filter and the user's face so that fragments of the filter do not come into contact with the user.

The cover layer 35 can be made of a material which is air permeable to allow filtered air to pass through from the filter 36 to the user. As an example, in one embodiment, a cover layer 35 is made of 220 thread-count Teflon coated cotton or satin can be used. Such a cover layer 35 may feel more comfortable or more familiar to the user. It may also act as a barrier between the filter and the user's face so that fragments of the filter do not come into contact with the user. Further, in some embodiments, a filter cover may include a hydrophobic composition or treatment. Such a composition can be applied to or included in the filter cover to provide stain- or water-resistant properties.

The cover layer 35 may attach to the plenum 30 at the edges of the filter 36 or it may extend over the edges of the filter 36 to attach beyond of the edges of the filter 36. Only a portion of the edge of the cover layer 35 may attach to the plenum 30, or the entire edge of the cover layer 35 may attach to the plenum. When the entire edge of the cover layer 35 is attached to the plenum 30, it encloses the filter 36 such that any fibers that detach from the filter 36 are encased within the space between the filter 36 and the cover layer 35, so that they do not come into contact with the user.

The cover layer 35 may be permanently attached to the plenum 30 such as by sewing or adhesive. Alternatively, the cover layer 35 may be removably attached to the plenum such as by hook and loop attachment or zippers. Removable attachment along a portion or all of the edge of the cover layer 35 may be desirable in embodiments in which the filter 36 is removable for washing or replacement, to allow access to the filter 36. In alternate embodiments, the cover layer 35 may be attached to the filter, which, in turn, attaches to the plenum. In such embodiments, the cover layer 35 may be sewn to the filter 36 or removably attached by any means such as the removable attachment mechanisms described for other embodiments. With this construction, the cover layer 35 forms part of the filter 36. Alternatively, the cover layer may be incorporated into a pillow case and not directly attached to the plenum, but adapted to slide over the plenum.

In some embodiments, air flow may be maintained across the plenum 30 through the use of rigid or semi-rigid support structures within the plenum 30. Such support structures would provide sufficient open space to allow air to flow through or around the structures. At the same time, they would be strong enough to prevent the plenum 30 from completely collapsing under the weight of a user's head.

The plenum is supported on the user's body and may have any shape. In the embodiment shown in FIGS. 1 and 7, the plenum is approximately U-shaped. When in use, the U-shaped plenum 30 is inverted such that the bottom of the U is oriented behind the neck of the user and forms the neck portion 37 (see FIG. 7) of the plenum 30. The plenum 30 includes an outer edge 42 around the outside and an inner edge 44 around the inside. Portions of the inner edge 44 at and near the neck portion 37 are close to, and may be in contact with, the user's neck. Two shoulder portions 38, 39 extend downward from the neck portion 37. As shown in FIG. 7, the shoulder portions 38, 39 extend across the front of the user's shoulders and may extend onto the front of the upper chest of the user. At least a portion of the upper surface 32 of the plenum 30 is air permeable, such as around the wearer's face. The plenum 30 of this embodiment is supported and held in position by wrapping around the user's neck and shoulders. Such embodiments may be used while sitting or may be used while lying in bed or while standing.

In alternative embodiments, the plenum is shaped like a bib. An example of such an embodiment is shown in FIG. 8. In this embodiment, the plenum 330 includes a chest portion 331. The lower surface of the chest portion 331 lies against the chest of the user. In an alternative embodiment, the plenum 330 also includes two shoulder portions adjoined to or extending upward from a top edge 346 of the chest portion 331. The shoulder portions extend up and over each of the user's shoulders. The shoulder portions may be shaped to extend toward each other behind the user's neck to hold the plenum 330 in place. In such embodiments, the shoulder portions may be somewhat flexible to allow them to flex when they are placed around the user's neck.

A bib-like plenum 330 may include one or more connectors 350 designed to extend from one side of the plenum to the other, behind the user's neck. Such a connector 350 may take the form of a strap or a pair of strings, for example. The connector may include a releasable attachment such as a snap, a hook and loop fastener or it may tie to hold the plenum 330 in place and to allow it to be put on and removed easily. As shown in FIG. 8, the connector 350 may attach to the plenum 330 at or near the top edge 346 of the chest portion 331. Alternatively, in embodiments in which the plenum 330 includes shoulder portions, a connector 350 may attach at or near the top edge of the shoulder portions.

In some embodiments of the invention, the filter may cover the entire upper surface of the plenum or it may be located at various locations on the upper surface of the plenum in order to provide filtered air which will be inhaled by the user. In one embodiment of a U-shaped plenum 30, such as that shown in FIG. 7, the filter covers the entire upper surface of the plenum. In another embodiment of a U-shaped plenum, the filter covers the upper surface 32 of both shoulder portions 38, 39, while the upper surface 32 of the neck portion 37 is impermeable. Alternatively, the filter may cover only a portion of the upper surface of each shoulder portion 38, 39. For example, the filter may form a strip adjacent to the inner edge 44 of a portion or all of each shoulder portion 38, 39, thus providing filtered air through the portions of the plenum 30 which are closest to the user's nose and mouth. The filter may be located only on the upper surface 32 of the plenum or it may wrap around the inner edge 44 of the plenum 30, partially extending onto the lower surface 34 of the plenum 30.

In embodiments in which the plenum 330 is bib shaped, such as that shown in FIG. 8, the filter may cover the entire upper surface 332 of the plenum 330. Alternatively, the filter may cover only part of the upper surface 332 of the chest portion 331 of the plenum 330. In another embodiment, the filter covers only a portion of the chest portion 331 of the plenum 330, such as the area adjacent to the top edge 346 of the chest portion 331 of the plenum 330 comprising approximately the upper half of the chest portion 331. Alternatively, the filter may cover less than half of the upper portion of the chest portion 331 of the plenum 330, such as the upper one third of the chest portion. In some embodiments, the filter is located only on the upper surface 332 of the plenum 330 which faces outward from the user's body. However, in some embodiments, the filter may also extend around the plenum 330 and onto the lower surface of the plenum 330, such as the portion of the lower surface which is adjacent to the top edge 346.

Figure 9:
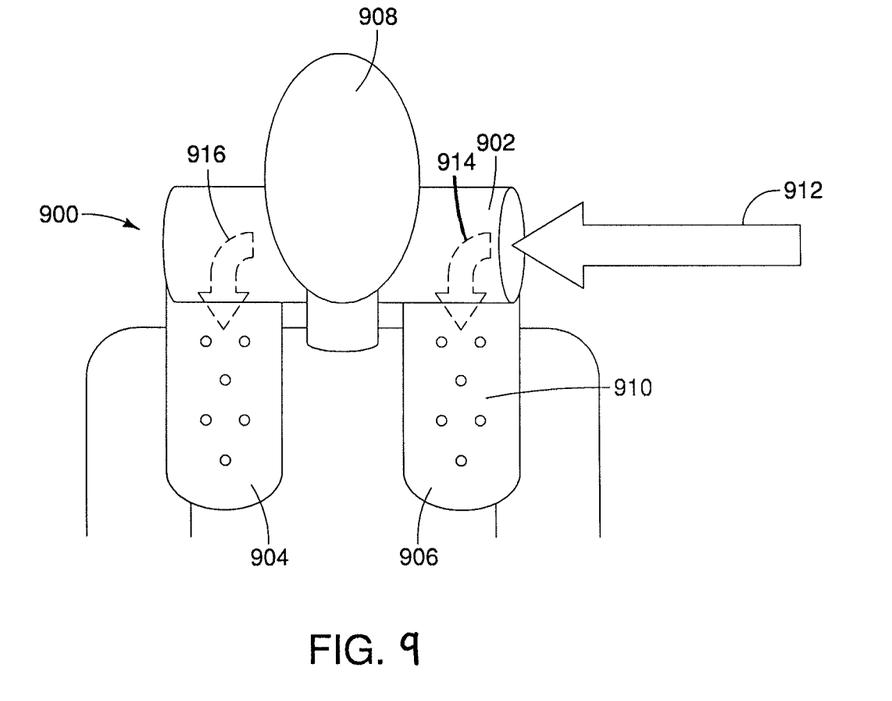
FIG. 9 is a top plan view of a plenum according to embodiments of the invention.

Alternative embodiments may include drape portions which can be draped over a user or a portion of a user to effectuate delivery of filtered air. An example of such an embodiment is shown in FIG. 9. In this embodiment, the plenum 900 includes a generally cylindrical neck portion 902 with two drape portions 904, 906 extending downward therefrom. The drape portions 904, 906 extend across the front of the shoulders and onto the front of the upper chest of the user 908 while the neck portion 902 remains behind the neck of the user 908. At least a portion of the upper surface 910 of the plenum 900 is air permeable, such as in the area around the user's face. In the embodiment shown in FIG. 9, the upper surfaces 910 of both drape portions 904, 906 are air permeable while the neck portion 902 is air impermeable. Additionally, in this embodiment, the lower surfaces of the drape portions (not shown) are air impermeable to direct maximum air flow through the air permeable upper surfaces 910. When the user 908 is sitting in a high backed chair, the lower surface of the neck portion 902 may rest on the chair back. Alternatively, the lower surface of the neck portion 902 may not rest on anything and the plenum 900 may be supported and held in position by wrapping around the user's neck and shoulders as shown. Such embodiments may be used while sitting or may be used while lying in bed. In use, the neck portion 902 serves as an air manifold, directing incoming air flow 912 to drape portions 904, 906 along arrows 914, 916 via internal air passages between the neck portion 902 and drape portions 904, 906. Air directed through such a plenum 900 can be pre-filtered air, i.e. air filtered prior to entering the plenum 900 as in an upstream blower, hose, or other filtering component. Alternatively, the air may be unfiltered air to be filtered within the plenum 900 prior to or as it is being dispersed through air permeable surface 910, such as for example, by a point of delivery filter.

In the foregoing detailed description, the invention has been described with reference to specific embodiments. However, it may be appreciated that various modifications and changes can be made without departing from the scope of the invention.

What is claimed is:

1. A neck-worn personal air filtration device for filtering aero-allergens from air flowing through the device, the device comprising:
    a blower adapted to provide an airflow;
    a collapsible U-shaped plenum comprising an upper surface and a lower surface, the upper and lower surfaces forming a neck portion and two chest portions, at least a portion of the upper surface of the plenum having an air permeable surface, the plenum being adapted to be worn about a neck of a user;
    a hose connecting the blower to the plenum; and
    a filter adapted to filter aero-allergen contaminants from the air flowing through the personal air filtration device, the blower being adapted to provide airflow to the plenum via the hose, the airflow being caused to accumulate within the plenum and exit the plenum through the air permeable surface.

2. The personal air filtration device of claim 1, wherein the filter comprises a point of delivery filter.

3. The personal air filtration device of claim 1, wherein the neck portion is adapted to be worn behind the neck of the user and the chest portions are adapted to be worn on a chest of the user.

4. The personal air filtration device of claim 3, wherein the air exiting through the air permeable surface is delivered to an area near a face of the user.

5. The personal air filtration device of claim 1, wherein the filter is removably attached to the plenum.

6. The personal air filtration device of claim 1, wherein the plenum comprises a single air chamber.

7. The personal air filtration device of claim 1, wherein the plenum comprises more than one interconnected air chamber.

8. The personal air filtration device of claim 1, wherein the lower surface comprises an air impermeable surface.

9. The personal air filtration device of claim 1, further comprising support structures within the plenum.

10. The personal air filtration device of claim 1, further comprising a generally air permeable cover.

11. The personal air filtration device of claim 1 wherein the filter is located on the upper surface.

12. The neck worn air filtration device of claim 1 wherein the upper surface and the lower surface are coupled together and form a substantially airtight connection between the upper and lower surfaces.

13. The neck worn air filtration device of claim 1, wherein the plenum is pressurized by the airflow to be filtered being caused to accumulate within the plenum, and wherein the air pressure in the plenum is configured to provide at least a portion of the support to the user's head or neck.

14. A method of providing aero-allergen filtered air to an area around a head of a user comprising:
    providing a plenum adapted to accumulate air comprising an upper surface and a lower surface, at least a portion of the upper surface being an air permeable surface and including a filter adapted to filter aero-allergen contaminants, the plenum being adapted to be worn about a neck of the user;
    providing a blower, the blower adapted to deliver air into the plenum; and
    delivering air to the plenum, thereby causing the air to pass through the filter and into the area around the head of the user.

15. The method of claim 14 further comprising accumulating air in the plenum to be filtered and delivered to a user such that the accumulated air to be filtered pressurizes the plenum, wherein the air pressurized in the plenum provides at least a portion of the support to the user's head or neck.

16. A neck worn air filtration device for filtering aero-allergens from an airflow comprising a collapsible U-shaped plenum, the plenum comprising:
    an upper surface, at least a portion of which is air permeable;
    a lower surface, wherein the upper and lower surfaces form a neck portion and two chest portions;
    an air inlet for connection to an air delivery hose; and
    a filter adapted to filter aero-allergen contaminants from air;
    wherein the plenum is adapted for receiving air through the inlet, accumulating air within the plenum, and delivering air through the air permeable surface as filtered air.

17. The neck worn air filtration device of claim 16 wherein the filter is located on the upper surface.

18. The neck worn air filtration device of claim 16 wherein the filter comprises the air permeable portion of the upper surface.

19. The neck worn air filtration device of claim 16 wherein the upper surface and the lower surface are coupled together and form a substantially airtight connection between the upper and lower surfaces.

20. The neck worn air filtration device of claim 16, wherein the plenum is pressurized by the airflow to be filtered, and wherein the air pressure in the plenum is configured to provide at least a portion of the support to the user's head or neck.

* * * * *